US010349910B2

(12) United States Patent
Zhong et al.

(10) Patent No.: US 10,349,910 B2
(45) Date of Patent: Jul. 16, 2019

(54) METHOD AND APPARATUS FOR ASSESSING BLOOD VESSEL STENOSIS (71) Applicants: AGENCY FOR SCIENCE, TECHNOLOGY AND RESEARCH, Singapore (SG); SINGAPORE HEALTH SERVICES PTE LTD, Singapore (SG)

(72) Inventors: Liang Zhong, Singapore (SG); Ru San Tan, Singapore (SG); Weimin Huang, Singapore (SG); Jiayin Zhou, Singapore (SG); Yuping Duan, Singapore (SG); Wei Xiong, Singapore (SG); Yanling Chi, Singapore (SG); Kyaw Kyar Toe, Singapore (SG)

(73) Assignees: AGENCY FOR SCIENCE, TECHNOLOGY AND RESEARCH, Singapore (SG); SINGAPORE HEALTH SERVICES PTE LTD, Singapore (SG)

(*) Notice: Subject to any disclaimer, the term of this patent is extended or adjusted under 35 U.S.C. 154(b) by 46 days.

(21) Appl. No.: 15/563,547

(22) PCT Filed: Mar. 30, 2016

(86) PCT No.: PCT/SG2016/050154
§ 371 (c)(1),
(2) Date: Sep. 29, 2017

(87) PCT Pub. No.: WO2016/159881
PCT Pub. Date: Oct. 6, 2016

(65) Prior Publication Data
US 2019/0029625 A1 Jan. 31, 2019

(30) Foreign Application Priority Data
Mar. 31, 2015 (SG) .......................... 10201502517P (51) Int. Cl.
*A61B 6/00* (2006.01)
*A61B 6/03* (2006.01)
(Continued)

(52) U.S. Cl.
CPC ........ *A61B 6/5217* (2013.01); *A61B 5/02007* (2013.01); *A61B 5/055* (2013.01);
(Continued)

(58) Field of Classification Search
CPC ... A61B 5/02007; A61B 5/055; A61B 5/1075; A61B 5/1076; A61B 5/489; A61B 6/032;
(Continued)

(56) References Cited

U.S. PATENT DOCUMENTS

2004/0223636 A1* 11/2004 Edic .................. G06T 7/0012
382/131

FOREIGN PATENT DOCUMENTS

WO WO 01/80185 A1 10/2001

OTHER PUBLICATIONS

PCT International Search Report for PCT Counterpart Application No. PCT/SG2016/050154, 4 pgs. (dated Jun. 9, 2016).
(Continued)

*Primary Examiner* — Manuchehr Rahmjoo
(74) *Attorney, Agent, or Firm* — Womble Bond Dickinson (US) LLP (57) ABSTRACT

A method for assessing blood vessel stenosis using image data of a subject is disclosed. The image data represents a vascular structure of the subject. The method comprises: (a) segmenting, from the image data, a vessel segment representing a segment of a blood vessel, (b) obtaining, using the image data, a plurality of two-dimensional images of the vessel segment; said plurality of two-dimensional images representing respective cross-sections of the vessel segment, (c) identifying, for each of the plurality of two-dimensional
(Continued)

images, a lumen area comprising lumen pixels representing a lumen of the corresponding cross-section, (d) obtaining a quantitative measure using the lumen areas of successive cross-sections of the vessel segment, and (e) assessing blood vessel stenosis using the quantitative measure. A computer system for performing the above method is disclosed.

18 Claims, 10 Drawing Sheets

(51) Int. Cl.
| | |
|---|---|
| G06T 7/00 | (2017.01) |
| A61B 5/02 | (2006.01) |
| A61B 5/055 | (2006.01) |
| A61B 5/107 | (2006.01) |
| A61B 5/00 | (2006.01) |
| G06T 7/12 | (2017.01) |
| G06T 7/62 | (2017.01) |
| A61B 8/12 | (2006.01) |

(52) U.S. Cl.
CPC .......... *A61B 5/1075* (2013.01); *A61B 5/1076* (2013.01); *A61B 5/489* (2013.01); *A61B 6/032* (2013.01); *A61B 6/504* (2013.01); *A61B 6/507* (2013.01); *A61B 8/12* (2013.01); *G06T 7/0012* (2013.01); *G06T 7/12* (2017.01); *G06T 7/62* (2017.01); *G06T 2207/10081* (2013.01); *G06T 2207/20168* (2013.01); *G06T 2207/30104* (2013.01); *G06T 2207/30172* (2013.01)

(58) Field of Classification Search
CPC ....... A61B 6/504; A61B 6/507; A61B 6/5217; A61B 8/12; G06T 2207/10081; G06T 2207/20168; G06T 2207/30104; G06T 2207/30172; G06T 7/0012; G06T 7/12; G06T 7/62
See application file for complete search history.

(56) References Cited

OTHER PUBLICATIONS

PCT Written Opinion for PCT Counterpart Application No. PCT/SG2016/050154, 6 pgs. (dated Jun. 9, 2016).
Rahil Shahzad, et al., "Automatic segmentation, detection and quantification of coronary artery stenosis on CTA," Int J Cardiovasc Imaging, vol. 29, No. 8, pp. 1847-1859 (2013).
Guanyu Yang, et al., "Quantitative measurement of coronary artery stenosis in CCTA images using a 2D parametric intensity model," Conf. Proc. IEEE Eng. Med. Biol. Soc., pp. 1071-1074 (Aug. 2014).
Armin Arbab-Zadeh, et al., "Quantification of Coronary Arterial Stenoses by Muitidetector CT Angiography in Comparison With Conventional Angiography," JACC: Cardiovascular Imaging, vol. 4, No. 2, pp. 191-202 (Feb. 2011).
Tim McInerney, at al., "Deformable models in medical image analysis: a survey," Medical Image Analysis, vol. 1, No. 2, pp. 91-108 (Jun. 1996).
Jieyin Zhou, et al., "Quantification of coronary artery Stenosis by Area Stenosis from cardiac CT angiography," Conf. Proc. IEEE Eng. Med. Biol. Soc., pp. 695-698 (Aug. 2015).
Sheoxiong Zhang, et at, "Accuracy of MDCT in assessing the degree of stenosis caused by calcified coronary artery plaques," Am J Roentgenol (AJR), vol. 191, No. 6, pp. 1676-1683 (Dec. 2008).
Graham Mowatt, et al., "64-Slice computed tomography angiography in the diagnosis and assessment of coronary artery disease: systematic review and meta-analysis," Heart, vol. 94, Iss. 11, 36 pgs. (Nov. 2008).
Jorg Hausleiter, et al., "Non-invasive coronary computed tomographic angiography for patients with suspected coronary artery disease: the Coronary Angiography by Computed Tomography with the Use of a Submillimeter resolution (CACTUS) trial," European Heart Journal, vol. 28, No. 24, pp. 3034-3041 (2007).
Daniel C. Peach, et al., "A systematic review of the clinical effectiveness of 64-slice or higher computed tomography angiography as an alternative to invasive coronary angiography in the investigation of suspected coronary artery disease," BMC Cardiovascular Disorders, vol. 11, No. 32, 11 pgs. (2011).
Alejandro F. Frangi, et al., "Multiscale vessel enhancement filtering," In Proc. of Medical Image Computing and Computer-Assisted Intervention, LNCS, vol. 1496, pp. 130-137 (1998).

* cited by examiner

METHOD AND APPARATUS FOR ASSESSING BLOOD VESSEL STENOSIS

CROSS-REFERENCE TO RELATED APPLICATIONS

This patent application is a U.S. National Phase Application under 35 U.S.C. § 371 of International Application No. PCT/SG2016/050154, filed on 30 Mar. 2016, entitled METHOD AND APPARATUS FOR ASSESSING BLOOD VESSEL STENOSIS, which claims priority to Singapore application No. 10201502517P, filed on 31 Mar. 2015.

TECHNICAL FIELD

The present disclosure relates to a method and apparatus for assessing stenosis in blood vessels, such as, but not limited to, coronary arteries.

BACKGROUND

Figure 1:
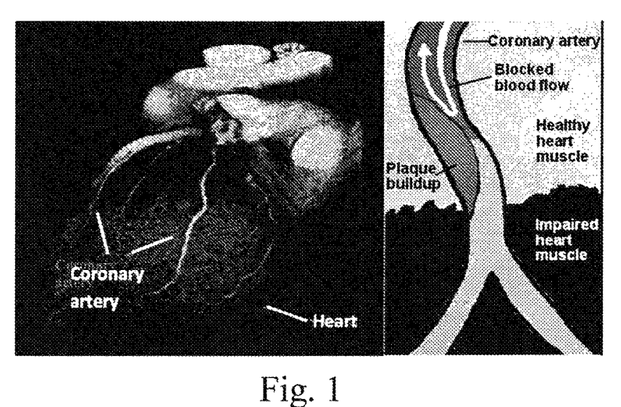
FIG. 1 shows an artery at the heart's anterior surface which has a narrowing lumen.

Coronary heart disease (CHD), affecting about 6% of general adult population, is a common cardiac disorder associated with coronary artery stenosis—the narrowing of coronary artery typically caused by a portion of the lumen of the coronary artery being blocked by plaque. For example, FIG. 1 shows an artery at the heart's anterior surface which has a narrowing lumen as a result of a build-up of cholesterol plaque at its inner wall. This causes a reduced blood supply to the heart.

In U.S., among populations aged more than 65 years old, the prevalence of CHD increases to 19.8% in 2010. CHD causes 1.2 million heart attacks annually and nearly 19% of deaths in US. In Singapore, cardiovascular disease (CVD) accounted for 30.4% of all deaths in 2011, among these, 19% are due to CHD. Therefore, timely and accurate evaluation of suspected CHD patients is among the keys to improving patient care, reducing costs and improving efficiency in care delivery.

Figures 2A, 2B:
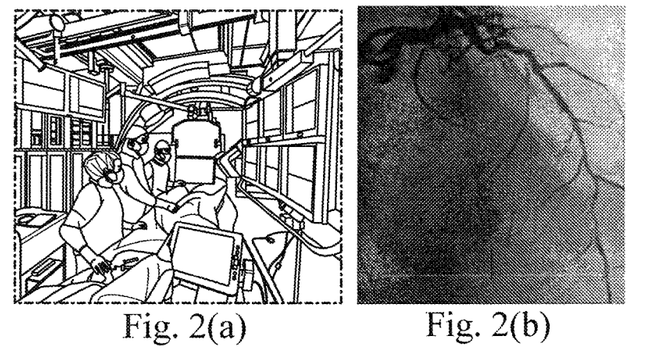
Figures 3A, 3B:
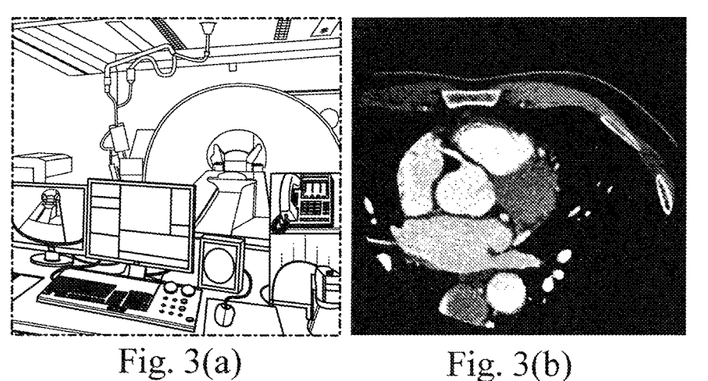

There are existing methods in assessing coronary artery stenosis. In particular, invasive coronary angiography (ICA) is the gold standard method for the delineation of anatomical coronary artery stenosis. FIG. 2 shows equipment used in ICA and a resultant image. Fractional flow reserve (FFR) measurement with pressure wire is the gold standard for the assessment of the physiological importance of an anatomical stenosis. The FFR measurement may be performed concurrently with ICA. Non-invasive computed tomography angiography (CTA) is a popular diagnostic alternative to ICA. In CTA, a sequence of two-dimensional (2D) images may be obtained by scans and a three-dimensional image volume (i.e. a stack of the 2D images) may be constructed. FIG. 3 shows equipment used in CTA and a resultant image. A brief comparison of advantages and disadvantages of these modalities is shown in Table 1 below.

TABLE 1

A comparison of ICA/FFR and CTA

| Modality | ICA and FFR measure | CTA |
| --- | --- | --- |
| Advantages | Accurate, current gold standard<br>Quantitative<br>Seamless connection with therapy | Outpatient examination<br>Non-invasive, easy to accept<br>Very high sensitivity<br>Low cost (~S$1,100 per exam) |

TABLE 1-continued

A comparison of ICA/FFR and CTA

| Modality | ICA and FFR measure | CTA |
| --- | --- | --- |
| Disadvantages | Inpatient procedure<br>Invasive, risk of complication<br>High cost (~S$6,000 per procedure)<br>Labor intensive (i.e. involves cardiologists, radiologists, technicians, and nurses) | Need expert interpretation<br>Less accurate, prone to over-rating |

Figure 4:
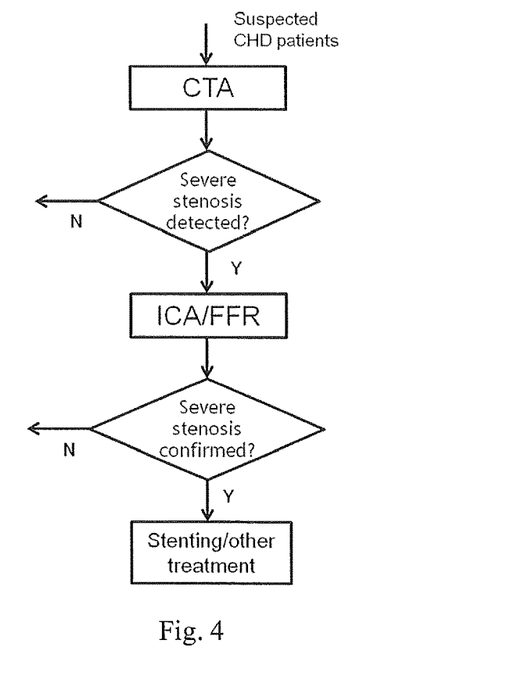
FIG. 4 is a flow chart illustrating the current standard clinical protocol for CHD patient care.

FIG. 4 is a flow chart illustrating the current standard clinical protocol for CHD patient care. CTA scan is performed on suspected CHD patients first. If severe artery stenosis is detected, a subsequent ICA/FFR will be performed. If the severity of the lesion is confirmed by ICA/FFR, stenting or other therapeutic intervention may be performed during the procedure.

CTA enables visualization of the coronary vessels in two-dimensional (2D) or three-dimensional (3D) formats but currently available CTA-based imaging techniques are limited in their abilities in assessing physiological stenosis. Currently, CTA data are interpreted by a radiologist or cardiologist and the severity of a coronary artery stenosis lesion is rated based on a parameter called percent Diameter Stenosis (DS). In particular, a range of DS is used, namely, <25%, 25-40%, 40-70%, >70%.

Figure 5:
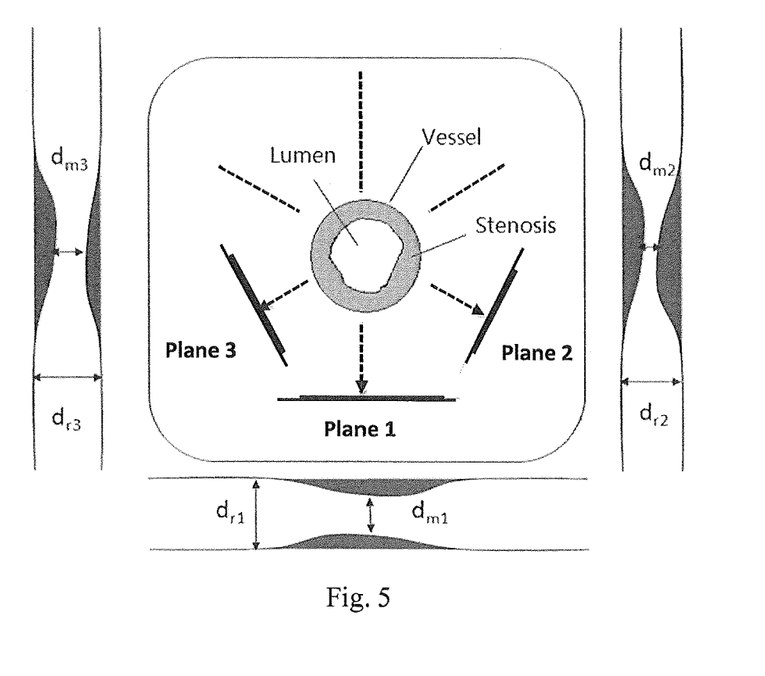
FIG. 5 illustrates the calculation of a percent Diameter Stenosis (DS) using 2D quantitative coronary angiography (QCA)

As illustrated by FIG. 5, DS is obtained by 2D quantitative coronary angiography (QCA), in which images are projected unto multiple planes and the arterial lumen diameter is assessed accordingly. Several clinical studies have reported that CTA has a very high sensitivity and negative prediction value in assessing coronary artery stenosis, but with a lower specificity and positive predication rate [1-4].

While CTA may be a reliable tool to rule out significant coronary artery stenosis, the CTA-based assessment of stenosis lacks precision. It requires an expert's interpretation of the image which may be subjective, and is often operator-dependent. This results in a significant number of false positive diagnoses or over-estimation, and often lead to unnecessary further tests (e.g. costly ICA and FFR) and/or treatments (e.g. stenting) being performed.

Therefore, it is desirable to provide an improved method and apparatus which provide a more accurate assessment of coronary artery stenosis.

SUMMARY

In general terms, the present disclosure proposes methods and apparatus which use a numerical measure (such as a measure indicative of an area of stenosis of the vessel) derived from lumen areas of successive cross-sections of a vessel segment to assess blood vessel stenosis.

According to a first expression, there is provided a method for assessing blood vessel stenosis using image data, such as computed tomography angiography (CTA) data, of a subject. The image data represents a vascular structure of the subject. The method typically comprises a computer processor performing:

(a) segmenting, from the image data, a vessel segment representing a segment of a blood vessel, (b) obtaining, using the image data, a plurality of two-dimensional images of the vessel segment; said plurality of two-dimensional images representing respective cross-sections of the vessel segment, (c) identifying, for each of the plurality of two-dimensional images, a lumen area comprising lumen pixels representing a lumen of the corresponding cross-section, (d) obtaining a quantitative measure using the lumen areas of successive cross-sections of the vessel segment, and (e) assessing blood vessel stenosis using the quantitative measure.

The present method utilizes a quantitative measure derived using lumen areas of successive cross-sections of a vessel segment. This may allow other lesion characteristics of stenosis (such as its length, shape and eccentricity) along a vessel segment to be taken into account when assessing vessel stenosis. For example, the effect of stenoses in series, which may greatly affect the blood flow, may be taken into consideration. Accordingly, the present method may allow automatic detection as well as quantification of blood vessel stenosis with greater accuracy and precision, and at a more holistic level. This provides more accurate, reproducible and informative indicators to the severity of stenosis for clinical decision making.

Operation (d) may comprise obtaining a profile of sizes of the lumen areas for the plurality of two-dimensional images corresponding to the successive cross-sections of the vessel segment.

The method may further comprise deriving, using the profile, a size of a restored lumen area for each of the cross-sections. The restored lumen area represents a lumen area when the vessel segment is stenosis-free, that is, as if the stenosis lesion had not been present or the lumen had been restored by removing the stenosis. This may be performed by a linear fitting of the profile followed by determining the size of the restored lumen area based on the fitted profile.

The method may comprise calculating a ratio of the size of the lumen area and that of the restored lumen area for at least one of the cross-sections.

The method may comprise identifying, from the plurality of images, a sub-set of images corresponding to cross-sections containing stenosis. The sub-set of images may be identified using the quantitative measure, for example, based on the ratio of the size of the lumen area and that of the restored lumen area calculated for the image.

The plurality of two-dimensional images may be obtained by first identifying a centerline for the segmented vessel, and extracting a series of two-dimensional images orthogonal to the centerline. The plurality of two-dimensional images may represent consecutive scans of cross-sections of the vessel at a regular interval, for example, at the interval of 1 mm apart along the centerline.

The centreline may be identified by extracting a minimal path within the vessel segment by minimizing a cost function. The cost function may define a path connecting two ends of the vessel segment.

Operation (c) may comprise identifying lumen boundary pixels for the lumen area using a gradient of intensity values of the pixels. For example, a plurality of diameter lines for the cross-section may be identified and for each diameter line, an intensity profile of intensity values for pixels lying on the diameter line is generated and the lumen boundary pixels are detected based on the intensity profile. In one embodiment, the lumen boundary pixels having a maximal gradient are identified as the boundary pixels.

Ellipse fitting of the identified lumen boundary pixels may be performed to obtain the lumen area, followed by further applying a deformable model.

Operation (a) typically comprises extracting a principle direction (i.e. the axial direction) of a geometrically tubular structure to segment the vessel or vessel segment.

The present disclosure may also be expressed as a computer system having a processor and a memory device configured to store program instructions operative, when performed by the processor, to cause the processor to perform a method described above.

The present disclosure may also be expressed as an apparatus configured to perform any one of the above methods. The apparatus is typically a computer system having appropriate hardware modules including an image segmentation module, an image generation module and an image analysis module configured to perform relevant operations as described above with reference to the respective methods.

In particular, there is provided a computer system for assessing blood vessel stenosis using image data of a subject. The image data represents a vascular structure of the subject. The computer system comprises:

an image segmentation module configured to segment, from the image data, a vessel segment representing a segment of a blood vessel, an image generation module configured to obtain, using the image data, a plurality of two-dimensional images of the vessel segment; said plurality of two-dimensional images representing respective cross-sections of the vessel segment, and an image analysis module configured to
identify, for each of the plurality of two-dimensional images, a lumen area comprising lumen pixels representing a lumen of the corresponding cross-section,
obtain a quantitative measure using the lumen areas of successive cross-sections of the vessel segment, and
assess blood vessel stenosis using the quantitative measure.

The various modules may be appropriately configured to further perform any additional operation of the methods described above.

It will be apparent to a skilled person in the art that the various hardware modules may be implemented by one or more computer processors that are in communication with memory devices storing program instructions. The memory devices may be, but is not limited to, random-access memory (RAM) and read-only memory (ROM). The one or more processors are configured to execute the program instructions so as to implement the functionality of the hardware modules. It is understood that by programming and/or loading executable instructions onto the computer system, at least one of the processors, the RAM, and the ROM are changed, transforming the computer system in part into a specific purpose machine or apparatus having the novel functionality taught by the present disclosure. It is fundamental to the electrical engineering and software engineering arts that functionality that can be implemented by loading executable software into a computer can be converted to a hardware implementation by well-known design rules. The computer system may be integrated with a device, such as an image acquisition device for acquiring images, such as a CT scanner, for performing CT angiography (CTA).

According to a further expression, there is provided a computer program product, such as a tangible recording medium. The tangible recording medium stores program instructions operative, when performed by a processor, to cause the processor to perform operations of the methods described above. The computer program product may be installed on a cloud of a loud computing system and may be configured to run on a remote server.

According to yet a further expression, there is provided a method for assessing blood vessel stenosis using image data of a subject. The image data comprises a plurality of two-dimensional images representing respective cross-sections of a vessel segment. The method comprises:

(a) identifying, for each of the plurality of two-dimensional images, a lumen area comprising lumen pixels representing a lumen of the corresponding cross-section, (b) obtaining a quantitative measure using the lumen areas of successive cross-sections of the vessel segment, and (c) assessing blood vessel stenosis using the quantitative measure.

In other words, the input image data of the above method may be a sequence of two-dimensional images which have already been appropriately processed to represent respective cross-sections with each being orthogonal to an axial direction of the vessel segment.

The present disclosure may also be expressed as a computer system having an image analysis module configured to perform the method. The computer system may be integrated with a device, such as an image acquisition device for acquiring images, such as a CT scanner, for performing CT angiography (CTA).

The term "automatic" is used in the document to mean that, although human interaction may initiate the algorithm, human interaction is not required while the algorithm is carried out.

It will be understood by a skilled person that, in this document, a reference to a cross-section in relation to a blood vessel, a vessel segment or the like which has a generally tubular structure, means a generally planar two-dimensional section transverse to an axial direction of the generally tubular structure.

The above-mentioned aspect of the present disclosure may be used in a method of treating a patient having blood vessel stenosis, for example, by surgery or therapy. More specifically, this method of treating the patient may comprise administering a treatment (such as a medicament or a stent) based on an assessment of blood vessel stenosis in the blood vessel of the patient, wherein the assessment is obtained using the above-mentioned aspect of the present disclosure.

The disclosure may alternatively be expressed as a computer system for performing such a method. This computer system may be integrated with a device, such as an image acquisition device for acquiring images. The invention may also be expressed as a computer program product, such as one recorded on a tangible computer medium, containing program instructions operable by a computers system to perform the operations of the method. The computer product may be installed on a cloud of a cloud computing system and may be configured to run on a remote server.

BRIEF DESCRIPTION OF THE DRAWINGS

Embodiments of the present invention will now be described for the sake of example only with reference to the following drawings, in which:

FIG. 2 is composed of FIG. 2(a) which shows equipment used in ICA, and FIG. 2(b) which shows a resultant image;

FIG. 3 is composed of FIG. 3(a) which shows equipment used in CTA, and FIG. 3(b) which shows a resultant image;

FIG. 6 is composed of FIG. 6(a) which is a flow diagram of an embodiment of the present method, and FIG. 6(b) which is a flow diagram illustrating sub-operations for identifying a lumen area in a cross-section according to an example;

FIG. 7 is composed of FIG. 7(a) which shows a cross-section of the vessel segment annotated with a diameter line and identified lumen boundary pixels.

FIG. 8 is composed of FIGS. 8(a) which shows a cross-sectional image of an artery, FIG. 8(b) which shows detected lumen boundary pixels, and FIG. 8(c) which shows the lumen area with ellipse fitting;

FIG. 10 is composed of FIG. 10(a) which shows segmentation of a coronary artery from a CTA dataset.

FIG. 11 is composed of FIG. 11(a) which shows a profile of sizes of the lumen area of successive cross-sections along a test vessel segment and lesions identified, and FIG. 11(b) which shows the lesions in the corresponding 2D and 3D CTA images; and FIG. 12 is composed of FIG. 12(a) which shows a profile of sizes of the lumen area of successive cross-sections along another test vessel segment and lesions identified, and FIG. 12(b) which shows the lesions in the corresponding 2D and 3D CTA images.

DETAILED DESCRIPTION

Method 100

Figure 6A:
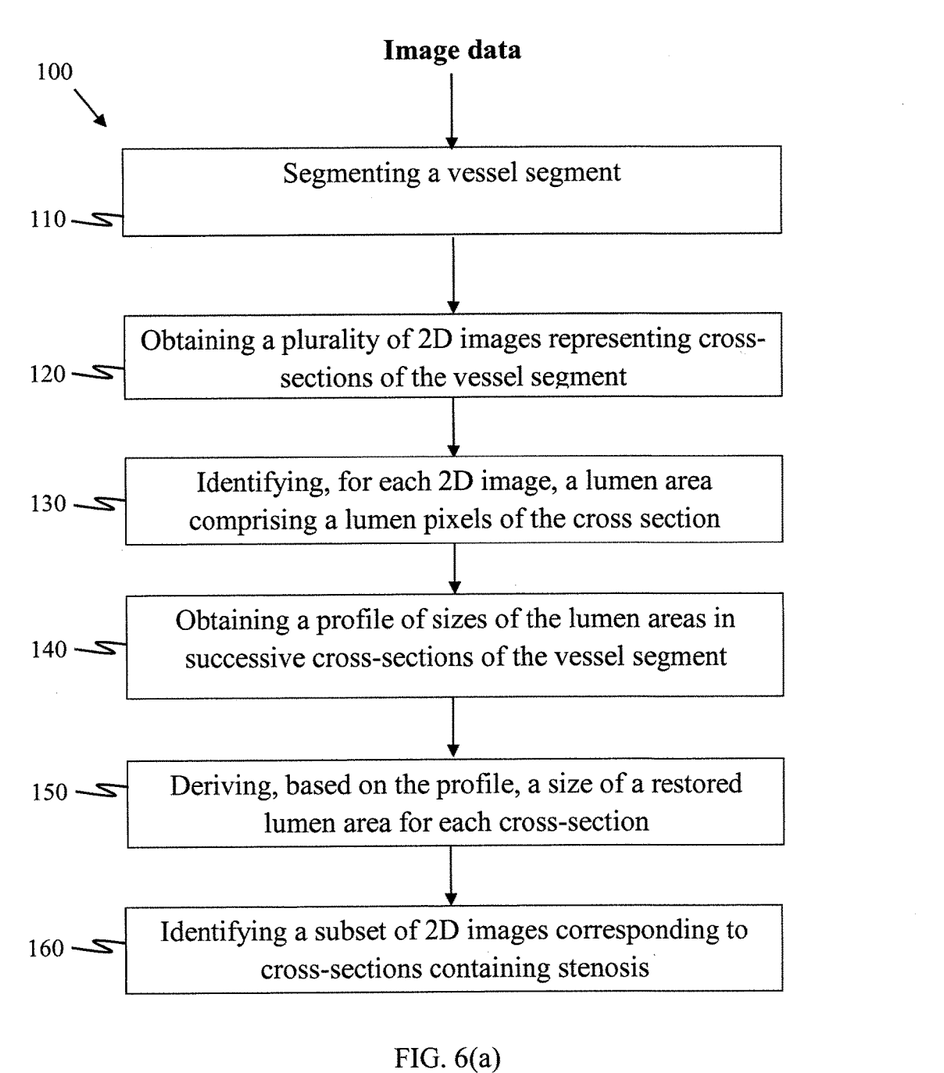

Referring to FIG. 6(a), the operations are illustrated of a method 100 which is an embodiment of the present disclosure and which assesses blood vessel stenosis of a human or animal subject. For example, the method 100 may be used to detect if blood vessel stenosis is present in the subject. The method 100 may also be used to quantify an extent of severity of blood vessel stenosis by, for example, a percent of area stenosis (AS) in one or more segments and/or cross-sections of the blood vessel.

The input to method 100 is image data representing at least a part of a vascular structure of the subject. For example, a three-dimensional image data set comprising a sequence of two-dimensional (2D) image scans of a subject's heart, acquired from coronary Computed Tomography Angiography (CTA).

As shown in FIG. 6(a), the method 100 comprises operations 110-160.

In operation 110, a vessel segment of a blood vessel in the vascular structure is segmented. In other words, pixels (in 2D image sequences) or voxels in (a 3D image volume) representing the blood vessel are identified from the image data.

In operation 120, a plurality of 2D images are generated from the image data. Typically, each of the 2D images represents a respective cross-section of the vessel segment, which is orthogonal to an axial direction of the vessel segment. The 2D image sequences may therefore represent consecutive scans of cross-sections of the vessel segment at an interval. For example, the interval may be a regular interval of 1 mm apart. Note that 2D image sequences may represent parallel, but typically non-parallel, cross-sections of the vessel segment, as the vessel segments are typically curved to a certain extent.

Figure 6B:
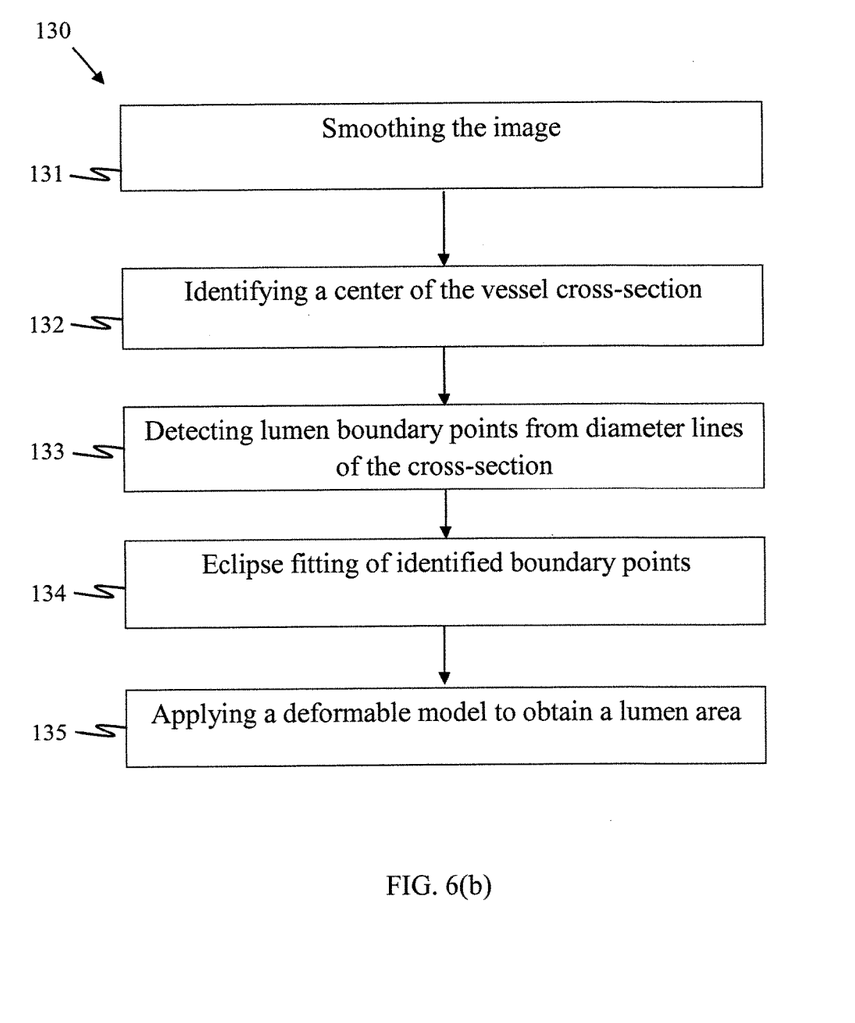

In operation 130, a lumen area is identified for each of the plurality of 2D images. The lumen area is identified as containing lumen pixels which represents the lumen structure of the blood vessel in that cross-section. The lumen area may be identified using sub-operations 131-135 as shown in FIG. 6(b), as will be described in more detail.

In operation 140, a profile of sizes of lumen areas identified in operation 130 for successive cross-sections of the vessel segment is obtained. The profile may be represented by a graphic representation such as a plot of the lumen area versus a relative position or sequence of each of the cross-sections. Note that a graphic representation is not necessary as it will be apparent to a skilled person that other form of representation of the profile is possible, such as by vectors.

In operation 150, a size of restored lumen area for each of the cross-sections may be estimated. This may be performed by deriving a second profile which describes sizes of restored lumen areas for the successive cross-sections based on the profile obtained in operation 140.

In operation 160, a subset of the plurality of 2D images may be identified as containing stenosis based on the size of the lumen area and restored lumen area of the corresponding cross-section. For example, if a comparison between the two areas exceeds a pre-defined threshold, then the cross-section may be identified as containing a stenosis lesion. The pre-define threshold may be a fixed value or be dependent upon another cross-section such a neighbouring cross-section.

Example Implementation of Method 100 for Assessing Coronary Artery Stenosis

The example below will be illustrated with respect to an assessment of coronary artery (including its branches) stenosis. It will be understood that the proposed methods may be applied to stenosis analysis for other types of vessels.

The imaging data described in the example below employs a CTA data of a patient. The CTA data is a three dimensional data describing a part of the coronary artery of the patient. The method proposes assessing the severity of coronary artery stenosis by obtaining a numerical measure using a profile of sizes of lumen areas in successive cross-sections of a vessel segment. In particular, the method derives data describing an area of stenosis in a cross-section of the coronary artery from the patient's CTA data. The example implementation of method 100 will now be described in more detail below.

Operation 110

The image data is processed to segment the blood vessel. In particular, pixels representing boundary of a blood vessel are identified.

The operation 110 may involve a sub-operation of pre-processing the image by enhancing the vascular features of the image. In this example, the vascular structures are enhanced using the multi-scale second order local structure (such as using a Hessian matrix in 2D or 3D). More specifically, a multi-scale vessel enhancement filtering proposed by Frangi et al is used [5]. The approach searches for geometrically tubular structures, which are detected by particular eigenvalue pattern analysis of the Hessian matrix (low value for $\lambda_1$ and high value for $\lambda_2$ & $\lambda_3$), thereby extracting a principle direction (i.e. an axial direction) along which the blood vessel extends. This enhances the contrast (or difference in pixel values) between vessel-like structures and other structures. By applying a suitable thresholding, coronary arteries can be segmented in the image.

Operation 120

A series of 2D images are obtained from the image data in this operation. Each of the 2D images represents a cross-section of the vessel such that the series of 2D images defines successive cross-sections along an axial direction of the blood vessel. In other words, each of the identified 2D images represents a cross-section plane of the blood vessel that is transverse to a longitudinal direction of the blood vessel.

In tubular structures, the eigenvector $e_1$ corresponding to the smallest eigenvalue $\lambda_1$ points in the longitudinal direction of the vessel, which has the smallest curvature and the normal plane to this direction (i.e., eigenvectors corresponding to $\lambda_2$ and $\lambda_3$) forms the cross-sectional plane to the vessel.

An artery or a portion of the artery may be used for the subsequent processing and analysis. For example, a user may specify segment of artery of interest by manually designating two endpoints on the segmented artery. In another possibility, the segment of interest may be automatically detected by a computer processor according to a pre-defined criterion, such as based on morphological landmarks of the blood vessel and/or a length of the vessel segment, etc.

A 3D path tracking for a centreline between the two fixed endpoints can be modelled into a minimal path problem. The centreline of the segmented vessel segment may be determined first for identifying the plurality of 2D images as images orthogonal to the centerline. The centreline may be extracted by solving a cost function describing a length of the path. By minimizing the cost function corresponding to the length of the path for which the integral of costs is minimum, a minimal path connecting the two endpoints may be obtained. The path is designated as the centreline and a sequence of 2D images representing the respective cross-sectional planes orthogonal to the centreline are obtained at an interval of 1 mm along the centreline.

Operation 130

Given the cross-sectional images of the vessel segment, it may still be challenging to extract the vessel lumen and to measure the stenosis in the images due to variations in image density and vessel curvatures (i.e. change in vessel radius), calcification, and bifurcations. The present inventors have developed an ellipse-based fitting procedure to estimate the lumen areas based on an extent of the change in pixel values (i.e. the gradient) at the vessel wall. The procedure has been shown to be able to extract the lumen area successfully. The below describes an embodiment for extraction of lumen areas from a 2D image and the method 100 includes performing the sub-operations below for the respective 2D images.

(i) Sub-Operation 131

For a 2D image I representing a vessel cross-section, a smoothing filter G is applied first to remove image noise (including pixels representing possible calcifications) to allow stenosis lesion including soft plaques to be more accurately identified. The possible calcification, which typically has an extremely high intensity values, is removed based on a naive Bayesian classification using training data. It will be understood by a person skilled in the art that the training data may be obtained, for example, by supervised machine learning using CTA images. The gradient L on the smoothed image is expressed as $L=|\Delta(G*I)|^2$. Suitable filters G may include a Gaussian filter, median filter, anisotropic diffusion filter, etc.

(ii) Sub-Operations 132, 133

Followed by the noise removal, a local peak point C, that is, a pixel with a maximum intensity value, can be located and identified as a center of the vessel section. One or more diameter lines passing through the center C of the vessel section are identified, and an intensity profile may be plotted for each of the diameter lines. For each of the diameter lines, the pixels corresponding to the maximal first derivative of the intensity profile are identified as lumen boundary pixels representing an edge of the lumen. In particular, two pixels may be identified for each diameter line from pixels located on each of the two sides of the center C.

The below provides an example of detecting lumen boundary points of a diameter line.

Figure 7A:
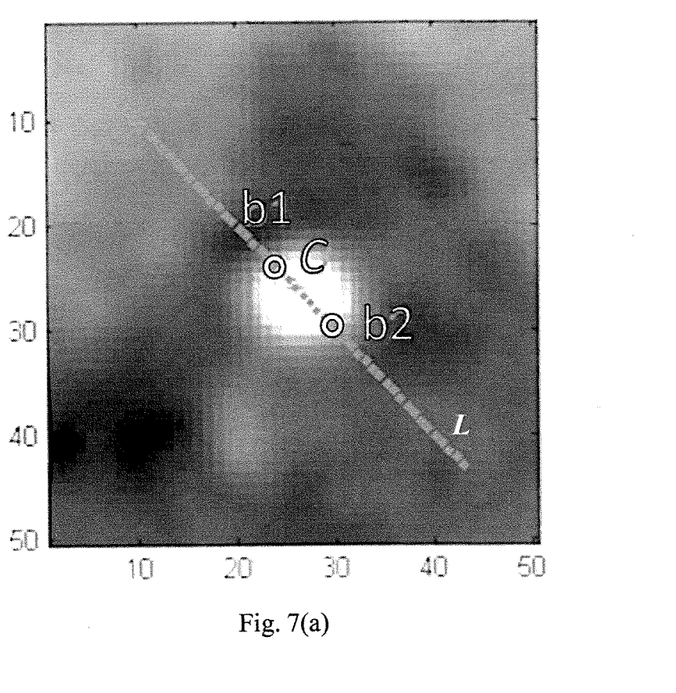
Figure 7B:
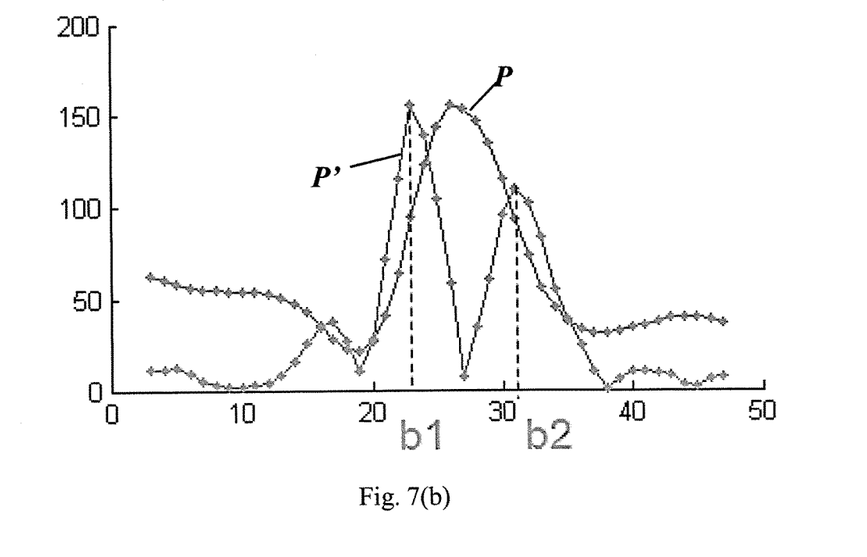
FIG. 7(b) shows an intensity profile for pixels lying on the diameter line from which the lumen boundary pixels are identified.

FIG. 7(a) shows a cross-section of the vessel segment annotated with a diameter line L and identified lumen boundary pixels b1, b2. In this example, the diameter line L passes through the lumen center C at an angle of $3\pi/4$. FIG. 7(b) shows an intensity profile P of intensity values for pixels lying on the diameter line L. A gradient profile P' representing changes in the pixel values is derived from the intensity profile P. It will be understood that this is equivalent to computing the first derivative of the intensity values. One pixel having a maximal gradient of the intensity value located on each side of C is identified as the lumen boundary pixels b1, b2. More lumen boundary pixels may be identified in a similar way from more diameter lines each oriented at respective angle of the cross-section.

Lumen edges may be identified from a plurality of diameter lines. In this example, lumen boundary points are obtained from 16 diameter lines. In particular, intensity profiles of pixels are obtained for diameter lines which are oriented from $0 \sim 2\pi$ at a uniform interval of $1/8 \pi$. More diameter lines may be used to sample more edge points, but this may increase computational costs.

(iii) Sub-Operation 134

Figures 8A, 8B, 8C:
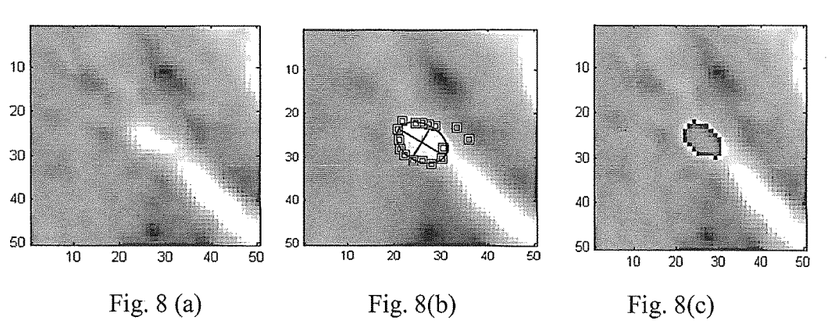

Due to the intensity variations around the vessel, the boundary points are not always distributed in a shape of a circle. FIG. 8(b) shows detected lumen boundary points for a cross-section image of an artery as shown in FIG. 8(a). The shape of the vessel lumen is then approximated using a circular or an elliptic fitting, as shown in FIG. 8(c). To eliminate the possible impact from vessel bifurcation, an inscribed ellipse or circle fitting is used to fit the detected boundary points towards the vessel as the vessel lumen.

(iv) Sub-Operation 135

The fitted vessel lumen can be further refined with deformable model such as snake, balloon, level sets, etc. With the ellipse or circle fitting as initialization, the segmentation is shown robust for the deformable models which are usually sensitive to the initialization. As the pixels for lumen area now identified, an area of the lumen may be identified accordingly, for example, based on a number of pixels representing the lumen.

By performing sub-operations 131-135 for each of the cross sectional images along the vessel segment, lumen areas of successive cross-sections of the vessel segment are obtained for further analysis in operations 140-160 below.

Operation 140

Figure 9:
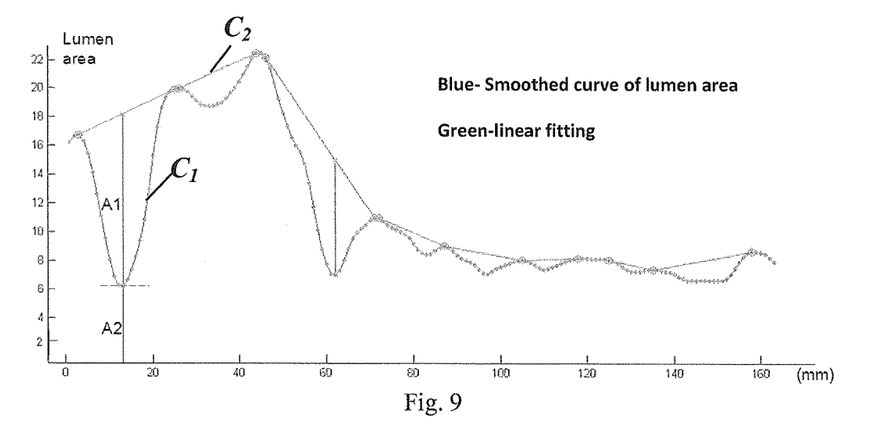
FIG. 9 shows a profile of sizes of the lumen areas of successive cross-sections along a vessel segment according to an example.

A profile indicative of stenosis in successive cross-sectional images along the vessel segment is derived in this operation. According to a particular example, a profile of sizes of the lumen areas for the plurality of 2D images corresponding to the successive cross-sections of the vessel segment is obtained. As shown in FIG. 9, a plurality of data points each representing an area of lumen of a particular cross-section are plotted and a curve $C_1$ connecting the data points is produced. The curve $C_1$ depicts a profile of the size of the lumen area along the successive cross-sections at an interval of 1 mm. The curve $C_1$ is smoothed using a median filter to minimize the effect of noise. Other filters may be used as will be apparent to a skilled person.

Operations 150-160

A sharp drop of the lumen area may suggest the presence of a stenosis lesion. In this example, the curve $C_1$ is used to derive a size of a restored lumen area for each of the cross-sections. The restored lumen area represents a lumen area as if the stenosis lesion had not been there or the lumen had been restored. A natural regression of the restored lumen area along a stenosis lesion-free vessel segment may be estimated by a linear fitting of the curve $C_1$ to derive a second profile $C_2$ as shown in FIG. 9. The curve $C_2$ represents the estimated sizes of restored lumen areas for the successive cross-sections.

Based on the curves $C_1$ and $C_2$, a subset of cross-sections are identified as containing or potentially containing stenosis. As shown in FIG. 9, A2 denotes the actual lumen area and A1+A2 represent the lumen area of the restored lesion-free artery. The cross-sections may be identified based on, for example, the size of the lumen area and the size of the restored lumen area of that cross-section. For example, a distance or separation (denoted as $A_1$ in FIG. 9) between the two curves $C_1$ and $C_2$, is indicative of a difference between the actual lumen area and the restored lesion-free lumen area. In other words, it may represent a deviation from a healthy state for the subject. According to a particular example, the sub-set of images are identified using the quantitative measure in a form of a ratio of the size of the lumen area and that of the restored lumen area calculated for the image.

If the quantitative measure exceeds a pre-defined threshold (e.g. is above or below a threshold value), then the cross-section may be identified as containing a stenosis lesion. The pre-define threshold may be a fixed value or be dependent upon another cross-section such a neighboring cross-section.

For a particular stenosis lesion, a numerical value is derived to quantify the stenosis by an area of stenosis (AS), and it is defined as $$AS=A1/(A1+A2)\times 100\%.$$

In another possibility, the quantitative measure may be the area of stenosis (AS) itself, which is equivalent to 1 minus the ratio of the size of the lumen area and that of the restored lumen area.

In another example, other characteristics of the stenosis such a length or its geometric profile may be estimated based on data derived from the lumen areas of successive cross-sections of the vessel segment.

Experimental Data and Results

The present inventors have demonstrated the implementation and performance of the present method using actual experimental data. The results are compared with some existing methods of assessing blood vessel stenosis as will be discussed below.

Specifically, cardiac CTA scans, which were perform using a dynamic volume scanner with a 320-row detector (Aquilion ONE, Toshiba Medical System), were collected from the National Heart Centre Singapore. The CTA scans were interpreted by a cardiologist and the percent diameter stenosis (DS) was given for each significant stenosis lesion.

For each CTA scan, the corresponding ICA was also collected and the percent DS was measured for each significant stenosis lesion by another cardiologist. The corresponding catheterized FFR measures were also recorded.

Figure 10A:
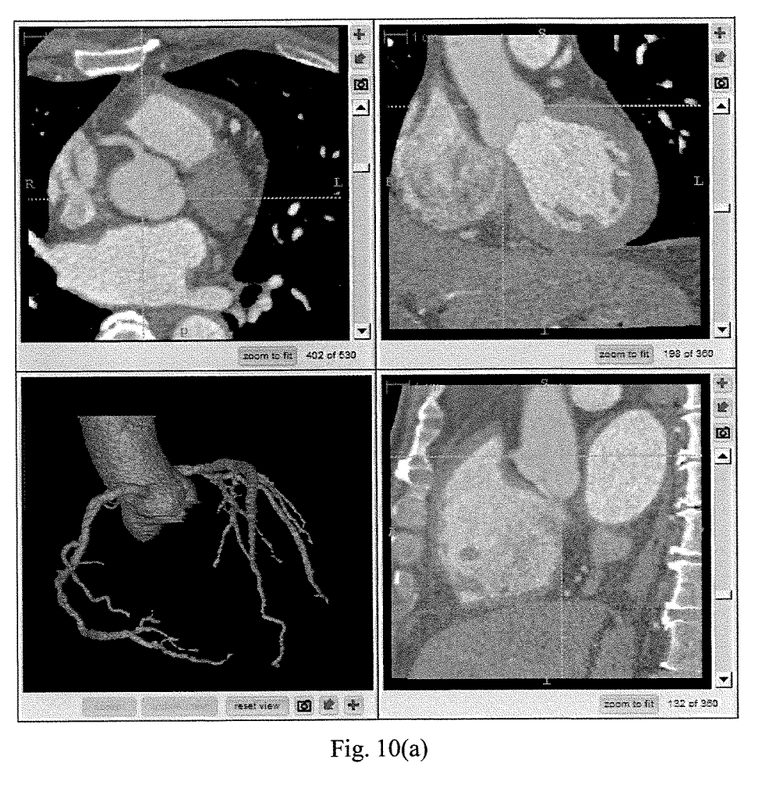
Figure 10B:
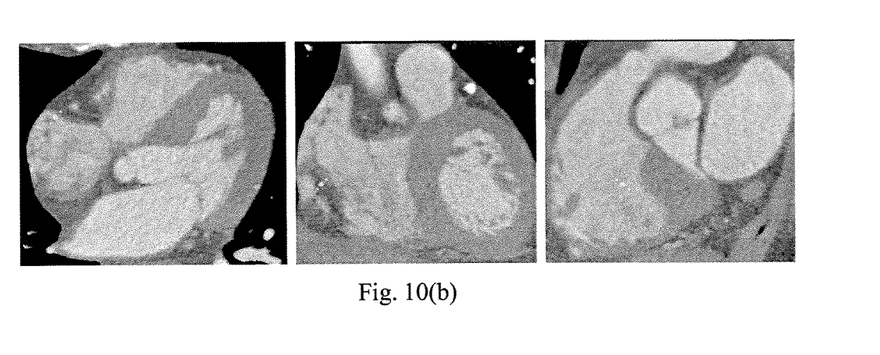
FIG. 10(b) shows identification of a centreline of the right coronary artery (RCA)
Figure 10C:
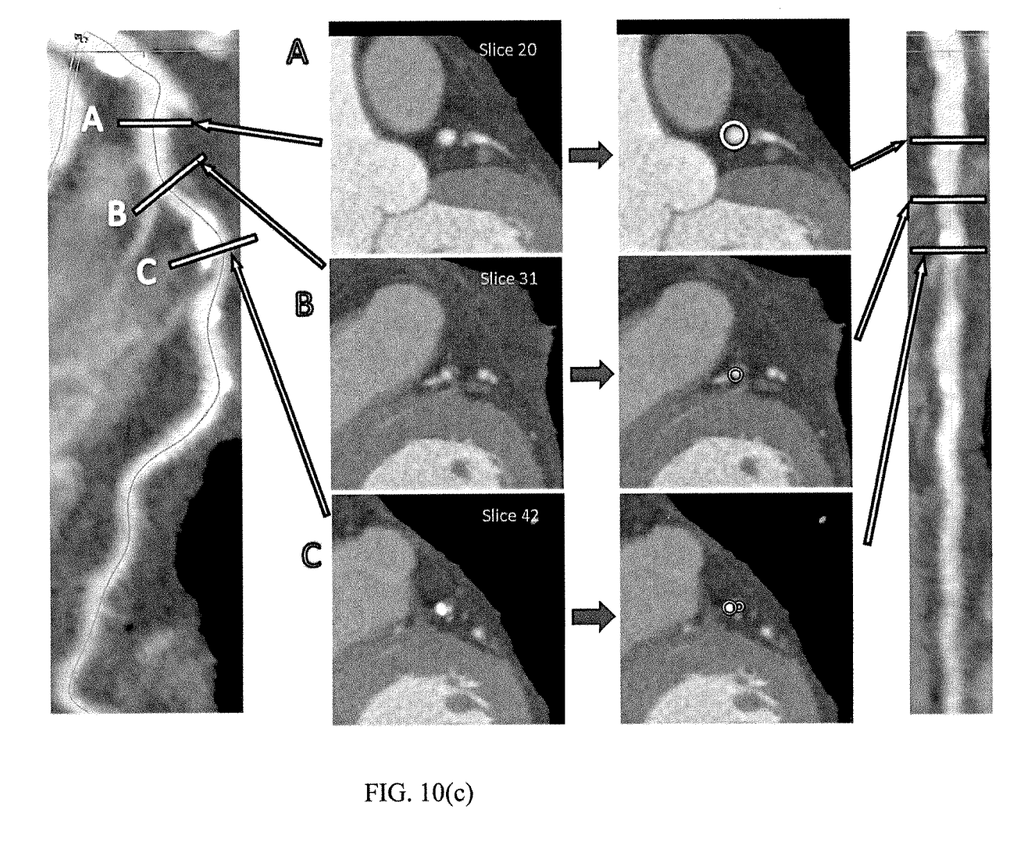
FIG. 10(c) shows a 2D projection of the RCA and its centreline by curved multi-planar reconstruction (cMPR) together with three 2D images representing respectively cross-sections.

FIG. 10(a)-(b) respectively show the segmentation of the coronary artery from the CTA dataset and identification of a centreline of the right coronary artery (RCA) using an embodiment of the present method. FIG. 10(c) shows a 2D projection of the RCA and its centreline by curved multi-planar reconstruction (cMPR). Three cross-sectional planes A, B, C along the vessel segment are identified from its proximal to distal end with their lumen areas shown before (the second column of FIG. 10(c)) and after segmentation (the third column of FIG. 10(c)).

Figure 11A:
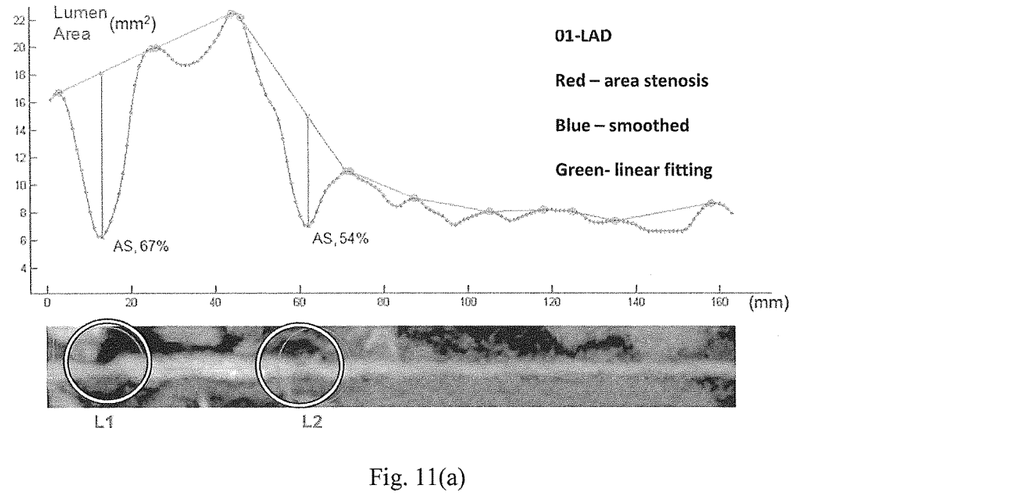
Figure 11B:
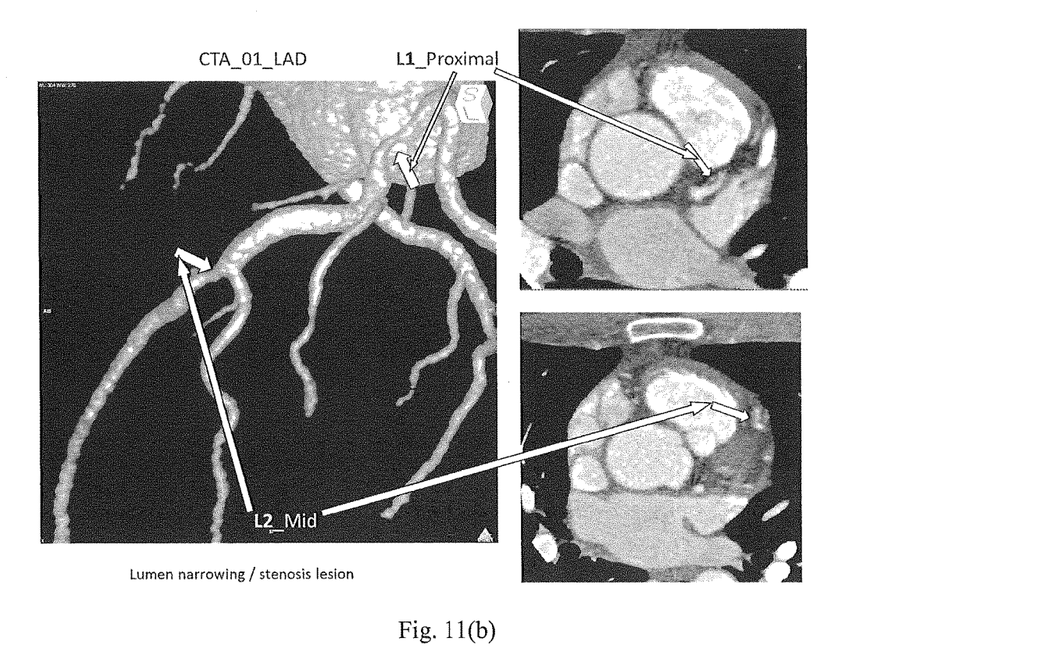

FIG. 11(a) shows a profile of the lumen area of the cross sections along a vessel segment which is the left anterior descending artery of a heart. Two lesions L1 and L2 are identified and quantified using the percent of area stenosis (AS). As shown, AS (in percentage form) of L1 in the proximal is 67% and that of L2 in the mid is 54%. The lesions L1 and L2 in the corresponding 2D CTA slices and 3D views are illustrated in FIG. 11(b).

Figure 12A:
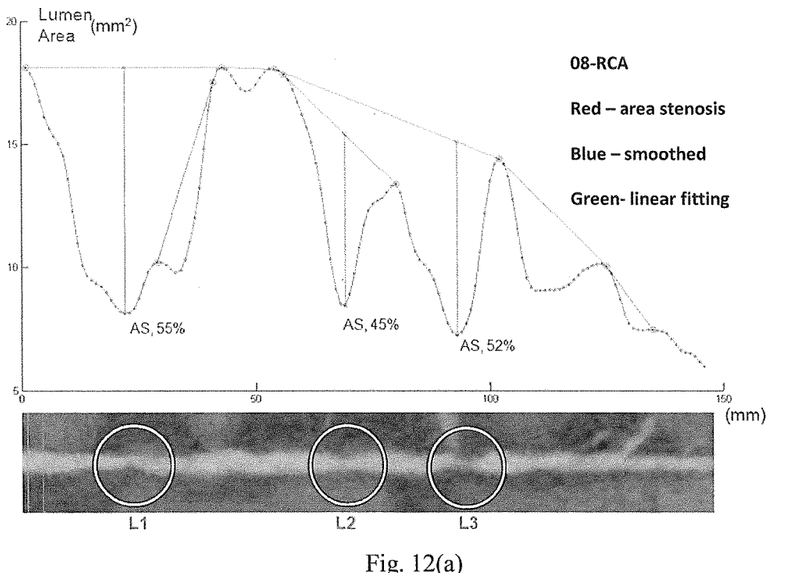
Figure 12B:
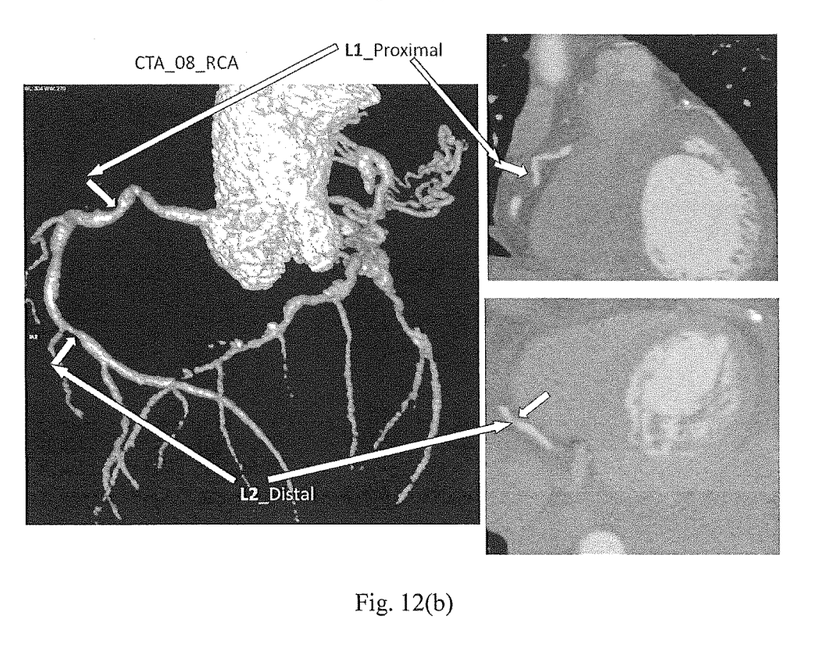

FIG. 12(a) shows a profile of the lumen area of the cross sections along a vessel segment which is the right coronary artery of a heart. Three lesions L1, L2 and L3 are identified and quantified using AS. As shown, AS (in percentage form) of L1 in the proximal is 55%, that of L2 in the mid is 45% and that of L3 in the distal is 52%. The lesions L1, L2 and L3 in the corresponding 2D CTA slices and 3D views are illustrated in FIG. 12(b).

Table 2 below shows results of detailed stenosis quantification for 9 coronary artery branches from 4 CTA data sets by AS (in bold). The corresponding DS measurement from CTA/ICA and FFR are tabulated for comparison as well.

TABLE 2

Stenosis quantified by present method (in bold) and the comparison with DS and FFR.

| CTA Data | Lesion location | CTA-DS | CTA-AS | ICA-DS | FFR |
|---|---|---|---|---|---|
| CT_01 | Proximal LAD | >70% | 67% | 70% | 0.85 |
| | Mid LAD | 40-70% | 54% | 70% | 0.74 |
| | Proximal RCA | 25-40% | 51% | 50% | |
| CT_02 | Proximal LAD | 50-69% | 64% | 60% | 0.85 |
| CT_06 | Proximal LAD | <25% | 37% | 30% | |
| | Mid LAD | 25-40% | 39% | 60% | 0.83 |
| | Distal LAD | >70% | 26% | | |
| | Proximal RCA | <25% | 25% | | |
| CT_08 | Proximal LAD | 50% | 66% | 70% | |
| | Proximal LCX | 40% | 53% | 50% | |
| | Proximal RCA | <40% | 55% | 30% | |
| | Distal RCA | 50-70% | 52% | 60% | 0.87 |
| CT_014 | Proximal LAD | 40-70% | 49% | 40% | 0.97 |

Advantages of Embodiments of Method 100 Over Existing Methods

It can be observed from Table 2 that the present method is able to more accurately and precisely quantify the severity of a stenosis lesion in coronary artery, as compared to using percent Diameter Stenosis (DS) from CTA.

DS is only a modest descriptor of coronary artery stenosis because DS does not incorporate other lesion characteristics such as a length, shape and eccentricity of the stenosis. Comparing to existing methods, the preferred embodiments also allow other lesion characteristics of stenosis along a vessel segment to assessed, by studying lumen areas of successive cross-sections of the segment. Therefore, the effect of stenoses in series may also be taken into consideration when assessing stenosis. In addition, the preferred embodiments utilize a profile of the size of lumen area to assess the extent of coronary artery stenosis. They provide an improved estimation of a lesion which is more consistent than using DS for studying vessel stenosis, because DS is susceptible to variations due to projection angles and subjective interpretation.

Overall, the proposed method and apparatus may provide more accurate, reproducible and informative indicators to the severity of stenosis thereby assisting clinicians in decision making for treatment and follow-up management. It can be deployed or integrated in a radiology reporting system at a hospital's radiology department, or in the workstation dedicated for cardiologist in the cardiology department. It can also be deployed in a mobile computing device and work in the operating theatre, for intra-operative review and reference.

Whilst the foregoing description has described exemplary embodiments, it will be understood by those skilled in the art that many variations of the embodiment can be made within the scope and spirit of the present invention. For example, the proposed method is not only suitable to process CTA image data but also works well on magnetic resonance angiography (MRA) and intra-vascular ultrasound (IVUS) image data.

REFERENCES

[1] Zhang S, Levin D C, Halpern E J, et al. Accuracy of MDCT in assessing the degree of stenosis caused by calcified coronary artery plaques. AJR Am J Roentgenol 2008; 191(6): 1676-1683.

[2] Mowatt G, Cook J A, Hillis G S, et al. 64-Slice computed tomography angiography in the diagnosis and assessment of coronary artery disease: systematic review and meta-analysis. Heart 2008; 96(11):1386-1393.

[3] Hausleiter J, Meyer T, Hadamitzky M, et al. Noninvasive coronary computed tomographic angiography for patients with suspected coronary artery disease: the Coronary Angiography by Computed Tomography with the Use of a Submillimeter resolution (CACTUS) trial. Eur Heart J 2007; 28(24):3034-3041.

[4] Paech D C, Weston A R. A systematic review of the clinical effectiveness of 64-slice or higher computed tomography angiography as an alternative to invasive coronary angiography in the investigation of suspected coronary artery disease. BMC Cardiovasc Disord 2011; 11:32.

[5] Frangi A, Niessen W, Vincken K, Viergever M. Multiscale vessel enhancement filtering. In Proc. of Medical Image Computing and Computer-Assisted Intervention. LNCS 1998; 1496:130-137.

What is claimed is:

1. A method for assessing blood vessel stenosis using image data of a subject, said image data representing a vascular structure of the subject, the method comprising:
   (a) segmenting, from the image data, a vessel segment representing a segment of a blood vessel,
   (b) obtaining, using the image data, a plurality of two-dimensional images of the vessel segment; said plurality of two-dimensional images representing respective cross-sections of the vessel segment,
   (c) identifying, for each of the plurality of two-dimensional images, a lumen area comprising lumen pixels representing a lumen of the corresponding cross-section, and identifying lumen boundary pixels for the lumen area using a gradient of intensity value of the pixel, and further comprising:
  (ci) identifying a plurality of diameter lines for the cross-section, and
  (cii) for each diameter line, obtaining an intensity profile of intensity values for pixels lying on the diameter line, and identifying the lumen boundary pixels based on the intensity profile,
(d) obtaining a quantitative measure using the lumen areas of successive cross-sections of the vessel segment, and
(e) assessing blood vessel stenosis using the quantitative measure.

2. The method according to claim 1, wherein the quantitative measure is indicative of an area of stenosis (AS) for at least one of the cross-sections of the vessel segment.

3. The method according to claim 2, further comprising deriving, using the profile, a size of a restored lumen area for each said cross-section.

4. The method according to claim 3, further comprising employing a linear fitting of the profile to derive the size of the restored lumen area of each said cross-section.

5. The method according to claim 3, further comprising calculating a ratio of the size of the lumen area and that of the restored lumen area for at least one of the cross-sections of the vessel segment.

6. The method according to claim 1, wherein operation (d) comprises obtaining a profile of sizes of the lumen areas for the plurality of two-dimensional images corresponding to the successive cross-sections of the vessel segment.

7. The method according to claim 1, further comprising identifying, from the plurality of images, a sub-set of images using the quantitative measure, said sub-set of images corresponding to cross-sections of vessel segment which contain stenosis.

8. The method according to claim 1, further comprising identifying a centerline for the vessel segment, said cross-sections being orthogonal to the centerline.

9. The method according to claim 8, further comprising extracting a minimal path within the vessel segment by minimizing a cost function defining a path connecting two ends of the vessel segment, wherein the centreline is identified based on the minimal path.

10. The method according to claim 1, further comprising identifying the lumen boundary pixels as pixels having a maximal gradient of the intensity value.

11. The method according to claim 1, further comprising ellipse fitting of the lumen boundary pixels to obtain the lumen area.

12. The method according to claim 11, further comprising applying a deformable model to the ellipse-fitted lumen area.

13. The method according to claim 1, wherein operation (a) comprises extracting a principle direction of a geometrically tubular structure thereby segmenting the vessel segment.

14. The method according to claim 1, wherein the image data is computed tomography angiography (CTA) data.

15. A computer system for assessing blood vessel stenosis using image data of a subject, said image data representing a vascular structure of the subject, wherein the computer system comprises:
  an image segmentation module configured to segment, from the image data, a vessel segment representing a segment of a blood vessel,
  an image generation module configured to obtain, using the image data, a plurality of two-dimensional images of the vessel segment; said plurality of two-dimensional images representing respective cross-sections of the vessel segment, and
  an image analysis module configured to:
  (a) identify, for each of the plurality of two-dimensional images, a lumen area comprising lumen pixels representing a lumen of the corresponding cross-section, and identify lumen boundary pixels for the lumen area using a gradient of intensity value of the pixel, and further configured to:
    (ai) identify a plurality of diameter lines for the cross-section, and
    (aii) for each diameter line, obtain an intensity profile of intensity values for pixels lying on the diameter line, and identify the lumen boundary pixels based on the intensity profile,
  (b) obtain a quantitative measure using the lumen areas of successive cross-sections of the vessel segment, and
  (c) assess blood vessel stenosis using the quantitative measure.

16. A non-transitory computer program product, such as a tangible recording medium, storing program instructions operative, when performed by a processor, to cause the processor to perform a method for assessing blood vessel stenosis using image data of a subject, said image data representing a vascular structure of the subject, the method comprising:
  (a) segmenting, from the image data, a vessel segment representing a segment of a blood vessel,
  (b) obtaining, using the image data, a plurality of two-dimensional images of the vessel segment; said plurality two-dimensional images representing respective cross-sections of the vessel segment,
  (c) identifying, for each of the plurality of two-dimensional images, a lumen area comprising lumen pixels representing a lumen of the corresponding cross-section, and identifying lumen boundary pixels for the lumen area using a gradient of intensity value of the pixel, and further comprising:
    (ci) identifying a plurality of diameter lines for the cross-section, and
    (cii) for each diameter line, obtaining an intensity profile of intensity values for pixels lying on the diameter line, and identifying the lumen boundary pixels based on the intensity profile,
  (d) obtaining a quantitative measure using the lumen areas of successive cross-sections of the vessel segment, and
  (e) assessing blood vessel stenosis using the quantitative measure.

17. A method for assessing blood vessel stenosis using image data of a subject, said image data comprising a plurality of two-dimensional images representing respective cross-sections of a vessel segment, the method comprising:
  (a) identifying, for each of the plurality of two-dimensional images, a lumen area comprising lumen pixels representing a lumen of the corresponding cross-section, and identifying lumen boundary pixels for the lumen area using a qradient of intensity value of the pixel, and further comprising:
    (ci) identifying a plurality of diameter lines for the cross-section, and
    (cii) for each diameter line, obtaining an intensity profile of intensity values for pixels lyinq on the diameter line, and identifyinq the lumen boundary pixels based on the intensity profile,
  (b) obtaining a quantitative measure using the lumen areas of successive cross-sections of the vessel segment, and (c) assessing blood vessel stenosis using the quantitative measure.

18. A computer system for assessing blood vessel stenosis using image data of a subject, the image data comprising a plurality of two-dimensional images representing respective cross-sections of a vessel segment, wherein the computer system comprises an image analysis module configured to:
- (a) identify, for each of the plurality of two-dimensional images, a lumen area comprising lumen pixels representing a lumen of the corresponding cross-section, and identify lumen boundary pixels for the lumen area using a gradient of intensity value of the pixel, and further configured to:
  - (ai) identify a plurality of diameter lines for the cross-section, and
  - (aii) for each diameter line, obtain an intensity profile of intensity values for pixels lying on the diameter line, and identify the lumen boundary pixels based on the intensity profile,
- (b) obtain a quantitative measure using the lumen areas of successive cross-sections of the vessel segment, and
- (c) assess blood vessel stenosis using the quantitative measure.

\* \* \* \* \*